United States Patent
Galeev

(10) Patent No.: US 9,510,788 B2
(45) Date of Patent: Dec. 6, 2016

(54) SYSTEMS AND METHODS FOR PROVIDING USER INSIGHTS BASED ON REAL-TIME PHYSIOLOGICAL PARAMETERS

(71) Applicant: Physical Enterprises, Inc., Vancouver (CA)

(72) Inventor: Artem Galeev, Kemerovo (RU)

(73) Assignee: Physical Enterprises, Inc., Vancouver, British Columbia (CA)

( * ) Notice: Subject to any disclaimer, the term of this patent is extended or adjusted under 35 U.S.C. 154(b) by 41 days.

(21) Appl. No.: 14/622,867

(22) Filed: Feb. 14, 2015

(65) Prior Publication Data

US 2015/0157256 A1   Jun. 11, 2015

(51) Int. Cl.
*A61B 5/00* (2006.01)
*A61B 5/0205* (2006.01)
*A61B 5/11* (2006.01)
*A61B 5/16* (2006.01)
*A61B 5/145* (2006.01)
*A61B 5/024* (2006.01)

(52) U.S. Cl.
CPC ............ *A61B 5/721* (2013.01); *A61B 5/0205* (2013.01); *A61B 5/1118* (2013.01); *A61B 5/165* (2013.01); *A61B 5/681* (2013.01); *A61B 5/0022* (2013.01); *A61B 5/02405* (2013.01); *A61B 5/02438* (2013.01); *A61B 5/1116* (2013.01); *A61B 5/14532* (2013.01); *A61B 5/4866* (2013.01); *A61B 5/4872* (2013.01)

(58) Field of Classification Search
CPC ....... A61B 5/681; A61B 5/0205; A61B 5/486; A61B 5/6801; A61B 5/6802; A61B 5/1118; A61B 5/1116; A61B 5/165; G08B 21/0446; G08B 21/0453
See application file for complete search history.

(56) References Cited

U.S. PATENT DOCUMENTS

| | | | |
|---|---|---|---|
| 2003/0208110 A1* | 11/2003 | Mault | A61B 5/0002 600/300 |
| 2014/0121540 A1* | 5/2014 | Raskin | A61B 5/6898 600/479 |
| 2015/0164349 A1* | 6/2015 | Gopalakrishnan | A61B 5/02405 600/508 |
| 2015/0182129 A1* | 7/2015 | Colley | A61B 5/0205 600/301 |

* cited by examiner

Primary Examiner — Robert N Wieland
(74) Attorney, Agent, or Firm — Clayton, McKay & Bailey, PC

(57) ABSTRACT

Described herein are systems and methods for monitoring physiological parameters in real time using a wrist-worn device, such as watch or bracelet. The physiological parameters may include heart rate variability, and the system may report conclusions to the user relating to stress and health, among other personalized messaging.

19 Claims, 9 Drawing Sheets

SYSTEMS AND METHODS FOR PROVIDING USER INSIGHTS BASED ON REAL-TIME PHYSIOLOGICAL PARAMETERS

FIELD OF THE DISCLOSURE

The embodiments relate generally to systems and methods that use non-invasive electro-optical technology for sensing and measuring physiological parameters and communicating a user over a web portal, and more specifically, systems and methods for communicating advertising and personalized content to a user based on the measured physiological parameters.

BACKGROUND

Many portable devices have been developed in which optical sensors are used to detect variation in blood flow through arteries or blood volume in subcutaneous tissue. Applications include the monitoring of heart rate, glucose level, apnea, respiratory stress, and other physiological conditions. The optical sensors often comprise one or more light sources that illuminate a targeted portion of the human body and one or more associated optical detectors that receive a portion of the optical energy emitted by the light sources.

One area of growing interest in the use of physiological monitors is with respect to personal wellness and/or physical exercise for purposes of fitness training, weight loss, or monitoring general health. Technological advances relating to optical sensors, signal processing, and display devices have made it possible to realize small, light-weight physiological monitors that can be embodied as devices that may be comfortably worn by a user. Such wearable devices may include, for example, wrist watches, bracelets, and arm bands.

The concept of highly targeted marketing on the internet has proven its efficacy. Today the most successful form of internet based advertising is the auction based, pay-per-click model. A newer form of internet target marketing is called behavioral marketing. Recent studies have shown that this model, where people's internet usage is followed and ads are presented to them in unfamiliar contexts, is proving to have significantly higher click through rates than contextual advertising in certain categories (i.e. finance).

A target market is Baby Boomers, ages 35-60. The preferred demographic is male in the majority, type A, in stressful, higher income level occupations and generally competitive. They are finding that they are not handling stress as well as they used to; they have started looking at ways to keep healthier so that they can live longer and better lives. Their wives are urging them to make "lifestyle" changes.

The definition of "lifestyle" is changing. A healthy lifestyle is now defined as attaining a delicate balance between nutrition, diet, physical condition, appearance and well-being. As the population ages, the baby boomer segment focuses on living a more healthy lifestyle. This new focus on lifestyle, along with better information, new product proliferation and channel buy-in is driving growth in the health and wellness market. In a recent Gallup Poll, 52% of those surveyed stated that improving their health and well-being was their top priority when it came to improving their overall health.

The market for health and lifestyle improvement products and services exceeds $220 billion, and is growing exponentially. The market for products that reduce stress and promote mental well-being is estimated at $20 billion annual revenue in the U.S.

In the early days of the Internet, search tools were needed by users to sort through the enormous amount of documents available to find those that were of interest. Search engines were invented to automate the process of sorting and ranking materials by relevance to a user. The search engines evolved, such as disclosed in Cohen, U.S. Pat. No. 6,067,539, which discloses an intelligent information retrieval system that finds matches to request with information, scores the relative merit of the matches, and displays the matches in ranked order. Websites used for searches such as www.yahoo.com, www.askjeeves.com, www.google.com, and others that utilize automated bots that collect information and use a stored index for rapid retrieval. The search engines include typical components (a) finder/locater of sources of information, (b) a source repository for storing the locations of information; (c) a sampler for sampling messages from the located source of information; (d) a matcher for determining a matching score for the retrieved message; and (e) a message repository for storing the retrieved message and the matching score.

Another patent is Rapaport, U.S. Pat. No. 5,890,152 for a Personal Feedback Browser For Obtaining Media Files that uses a personal profile database obtaining media files from the internet. Selected media files are displayed based on user-specified information stored in the personal profile database, which includes, the interests, attitude/aptitude, reading comprehension and tastes of a user.

Another patent, Bair, U.S. Pat. No. 6,003,024, which discloses a system and method for selecting rows from dimensional databases as those databases are expanded with more data associated with time in a manner that creates yet another table that allows searching for data rows that are collected over a time series Temporal query primitive functions may then be applied to the dimension tables in a manner that permits comparison of events and data that changes over time. Of particular interest in this patent is the activity of a person viewing media, typically a files or pages on a website and the sequence of files viewed and actions performed that leads toward a purchase of a product or service.

There is a need to know how one is doing from a health perspective. In some individuals, there is a daily, even hourly, need to know one's health. The prior art has provided some devices to meet this need.

Various devices can be used to collect physiological data from an individual. One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

The major advantages of pulse oximetry devices include the fact that the devices are non-invasive, easy to use, allows for continuous monitoring, permits early detection of desaturation and is relatively inexpensive. The disadvantages of pulse oximetry devices are that it is prone to artifact, it is inaccurate at saturation levels below 70%, and there is a minimal risk of burns in poor perfusion states. Several factors can cause inaccurate readings using pulse oximetry including ambient light, deep skin pigment, excessive motion, fingernail polish, low flow caused by cardiac bypass, hypotension, vasoconstriction, and the like.

Chin et al., U.S. Pat. No. 6,018,673 discloses a pulse oximetry device that is positioned entirely on a user's nail to reduce out of phase motion signals for red and infrared wavelengths for use in a least squares or ratio-of-ratios technique to determine a patient's arterial oxygen saturation.

Smith, U.S. Pat. No. 4,800,495 discloses an apparatus for processing signals containing information concerning the pulse rate and the arterial oxygen saturation of a patient. Smith also discloses maintaining the position of the LEDs and detectors to prevent motion-artifacts from being produced in the signal.

Another method for using a pulse oximeter to measure blood pressure is disclosed in U.S. Pat. No. 6,616,613 to Goodman for a 'Physiological Signal Monitoring System'. The '613 patent discloses processing a pulse oximetry signal in combination with information from a calibrating device to determine a patient's blood pressure.

Chen et al, U.S. Pat. No. 6,599,251 discloses a system and method for monitoring blood pressure by detecting pulse signals at two different locations on a subjects body, preferably on the subject's finger and earlobe. The pulse signals are preferably detected using pulse oximetry devices.

Schulze et al., U.S. Pat. No. 6,556,852, discloses the use of an earpiece having a pulse oximetry device and thermopile to monitor and measure physiological variables of a user.

Malinouskas, U.S. Pat. No. 4,807,630, discloses a method for exposing a patient's extremity, such as a finger, to light of two wavelengths and detecting the absorbance of the extremity at each of the wavelengths.

Jobsis et al., U.S. Pat. No. 4,380,240 discloses an optical probe with a light source and a light detector incorporated into channels within a deformable mounting structure which is adhered to a strap. The light source and the light detector are secured to the patient's body by adhesive tapes and pressure induced by closing the strap around a portion of the body.

Tan et al., U.S. Pat. No. 4,825,879 discloses an optical probe with a T-shaped wrap having a vertical stem and a horizontal cross bar, which is utilized to secure a light source and an optical sensor in optical contact with a finger. A metallic material is utilized to reflect heat back to the patient's body and to provide opacity to interfering ambient light. The sensor is secured to the patient's body using an adhesive or hook and loop material.

Modgil et al., U.S. Pat. No. 6,681,454 discloses a strap that is composed of an elastic material that wraps around the outside of an oximeter probe and is secured to the oximeter probe by attachment mechanisms such as Velcro, which allows for adjustment after initial application without producing excessive stress on the spring hinge of the oximeter probe.

Diab et al., U.S. Pat. No. 6,813,511 discloses a disposable optical probe suited to reduce noise in measurements, which is adhesively secured to a patient's finger, toe, forehead, earlobe or lip.

Diab et al., U.S. Pat. No. 6,678,543 discloses an oximeter sensor system that has a reusable portion and a disposable portion. A method for precalibrating a light sensor of the oximeter sensor system is also disclosed.

Tripp, Jr. et al., U.S. Statutory Invention Registration Number H1039 discloses an intrusion free physiological condition monitor that utilizes pulse oximetry devices.

Hisano et al., U.S. Pat. No. 6,808,473, discloses a headphone-type exercise aid which detects a pulse wave using an optical sensor to provide a user with an optimal exercise intensity.

Mathews, U.S. Pat. No. 5,431,170 ("Mathews"), discloses a pulse responsive device, which has a pulse oximetry device (10) attached to a headband (12) and a separate read-out device (14) that may be attached to a glove and worn on the user's hand. Mathews discloses that the read-out device (14) has a digital display and an analogue display, however, Mathews provides no further detail.

Mault et al, U.S. Patent Application Publication No. 2002/0109600 ("Mault") discloses a smart activity monitor ("SAM") which is a pedometer based device which includes an electronic clock, a sensor, entry means for recording food consumption and exercise activities and a memory for storing such information. Mault fails to disclose the details of the display other than to mention that the SAM has a time display, an exercise display and a food display, with the exercise and food displays having a bar-graph style. Mault fails to disclose an optical sensor in detail, and only states that photo-plethysmography may be used to determine the heart rate by a sensor provided on the rear of a wrist mounted SAM.

Kopotic et al, U.S. Pat. No. 6,470,199, discloses a sock for positioning an optical probe.

Yasukawa et al., U.S. Pat. No. 5,735,800, discloses a wrist-worn device which is intended for limited motion about the user's wrist. Yasukawa discloses an optical sensor that uses a blue LED with a phototransistor in conjunction with an analog to digital converter to provide a digital signal to a data processing circuit.

However, the prior art fails to provide a method or system that allows for real-time physiological data of a user to be utilized to provide the user with advertising or personalized content communications based on the real-time physiological data of a user.

Therefore, a need exists for improved physiological monitoring devices.

SUMMARY OF THE DISCLOSURE

In one embodiment, the system may continuous test physiological parameters of a user, including periodic recording of heart rate variability, to assess stress level and physical fitness of users. The assessment may be carried out automatically during user's usual daily physical activity.

The system may accomplish the assessment by using a wrist-worn device such as a bracelet or watch to collect data from different sensors (movements, time, illumination, atmosphere pressure and any others). Based on the sensor data, a processor in the system (on the wrist-word device or on a server) then identifies patterns of user's activity, such as sitting, walking, jogging, driving, television watching and others. The wrist-worn device can ask the user for help with identification of patterns in one embodiment.

The wrist-worn device and/or server may look for the known patterns in real time. If a pattern appears and is recognized, the wrist-worn device may switch on heart rate variation (HRV) recording. The server may compare HRV data of the same patterns day by day and recognize declining or improving stress level and physical fitness levels in the individual.

An embodiment may collect information about the user's heart or other physiological data. Alternatively, the present invention utilizes other internet applications and tests to collect all types of physiological data for a user through various interface devices (body fat scales, activity monitors, galvanic skin sensors, glucose monitors, etc.). This data is then used to generate a communication for the user based on the collected data. The communication is preferably an advertisement or personalized content, and is delivered in a timely manner while the user is receptive to receiving the communication.

The above and further objects, features and advantages thereof will be recognized by those skilled in the pertinent art from the following detailed description of the invention when taken in conjunction with the accompanying drawings.

It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

DESCRIPTION OF THE EMBODIMENTS

Figure 1:
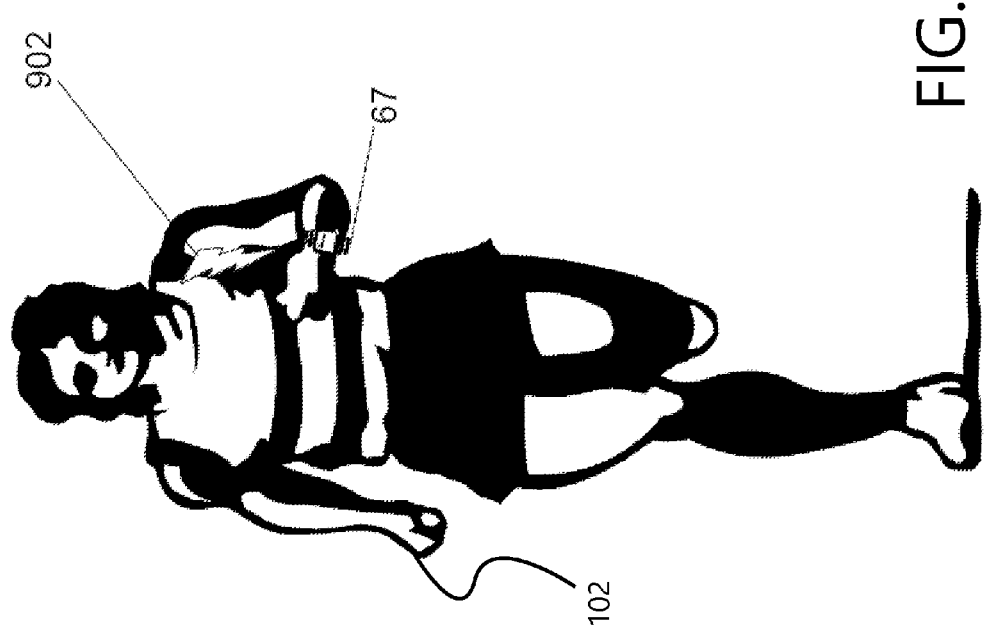
FIG. 1 is an example image of a jogger wearing a device for obtaining and transmitting real-time physiological data in accordance with an embodiment.

Disclosed herein are embodiments of an apparatus for sensing, measuring, and displaying physiological information. In one embodiment, the system may continuous test physiological parameters of a user, including periodic recording of heart rate variability, to assess stress level and physical fitness of users. The assessment may be carried out automatically during user's usual daily physical activity.

The system may accomplish the assessment by using a wrist-worn device such as a bracelet or watch to collect data from different sensors (movements, time, illumination, atmosphere pressure and any others). Based on the sensor data, a processor in the system (on the wrist-word device or on a server) then identifies patterns of user's activity, such as sitting, walking, jogging, driving, television watching and others. The wrist-worn device can ask the user for help with identification of patterns in one embodiment.

The wrist-worn device and/or server may look for the known patterns in real time. If a pattern appears and is recognized, the wrist-worn device may switch on heart rate variation (HRV) recording. The server may compare HRV data of the same patterns day by day and recognize declining or improving stress level and physical fitness levels in the individual.

In one aspect, the apparatus may comprise an optical sensor incorporated into a wearable device. The optical sensor may be incorporated at a location of the wearable device such that, in use, a surface of the optical sensor may be adjacent or in close proximity to a targeted area of a user's body. In one embodiment, the optical sensor may comprise one or more light sources for emitting light proximate the targeted area and one or more optical detectors for detecting reflected light from the targeted area.

In one embodiment, the physiological information may be heart rate information. In other embodiments, the physiological information may be blood pressure information. Alternatively, the physiological information may be any information associated with a physiological parameter derived from information received by the wearable device. Regardless, the physiological information may be used in the context of, for example, athletic training, physical rehabilitation, patient monitoring, and/or general wellness monitoring. Of course, these examples are only illustrative of the possibilities and the device described herein may be used in any suitable context.

While the systems and devices described herein may be depicted as wrist worn devices, one skilled in the art will appreciate that the systems and methods described below can be implemented in other contexts, including the sensing, measuring, and display of physiological data gathered from a device worn at any suitable portion of a user's body, including but not limited to, other portions of the arm, other extremities, the head, and/or the chest.

Reference will now be made in detail to certain illustrative embodiments, examples of which are illustrated in the accompanying drawings. Wherever possible, the same reference numbers will be used throughout the drawings to refer to the same or like items.

Heart rate variability ("HRV") is a physiological phenomenon of fluctuations of time intervals between heartbeats, and may be measured in an embodiment described herein. Based on HRV measurements in addition to other collected data, an embodiment herein may provide insights and analysis to a user.

FIG. 1 illustrates a runner 102 wearing a physiological monitoring device 67 which obtains real-time physiological data for the runner, and processes stores that data on the device 67 or a separate device. The data can then be sent via transmission 902 over a network to a web portal for analysis in an embodiment. The runner subsequently receives a communication based on the analyzed physiological data in the form of an advertisement or personalized content.

Figure 2:
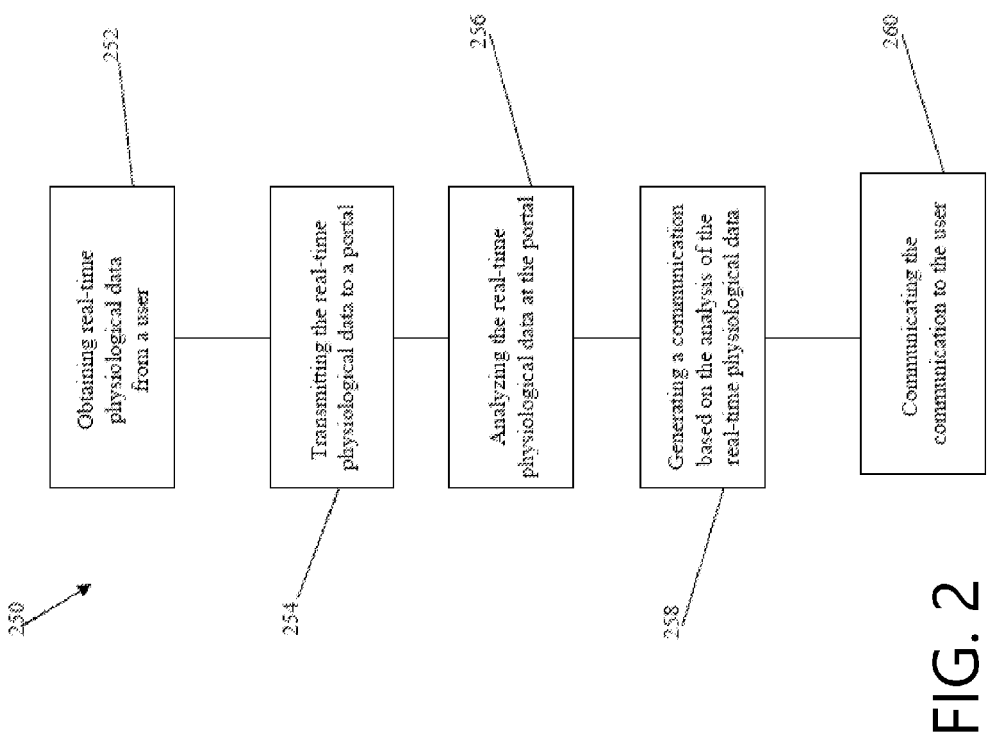
FIG. 2 is an exemplary flow chart in accordance with an embodiment.

FIG. 2 is an example flow chart of a method 250 utilized in one embodiment. At step 252, real-time physiological data for a user is obtained using a physiological monitor device. Several different devices may be used to obtain physiological data. For example, to obtain heart rate, pulse oximeters, pseudo-pulse oximeters, EKG devices, and other known devices may be used. Dickinson, U.S. Pat. No. 6,675,041, for an Electronic Apparatus And Method For Monitoring Net Calorie Intake, discloses such a device and is hereby incorporated by reference in its entirety.

Exemplary methods of obtaining physiological data useful with the present invention are disclosed in U.S. Patent Publication Number 2005/0251056, U.S. Patent Publication Number 2005/0251055, U.S. Patent Publication Number 2005/0251054, U.S. Patent Publication Number 2005/

0251057, U.S. Patent Publication Number 2005/0251051, U.S. Patent Publication Number 2005/0251424, all of which are hereby incorporated by reference in their entireties.

Continuing with FIG. 2, at step 254 the physiological data may be transmitted to a web portal over a network.

At step 256, the physiological data is analyzed, typically at a server for the web portal.

At step 258, based on the analysis of the physiological data, a communication is generated for the user. The communication is an advertisement or a personalized content based on the analysis of the physiological data.

At step 260, this communication is communicated to the user. Preferably, the communication is transmitted to the user is a similar fashion as the transmission of the real-time physiological data. Alternatively, the communication is sent to the user using another communication means such as email, text-message to a mobile telephone or personal digital assistant ("PDA"), postal mail, or the like.

Figure 3:
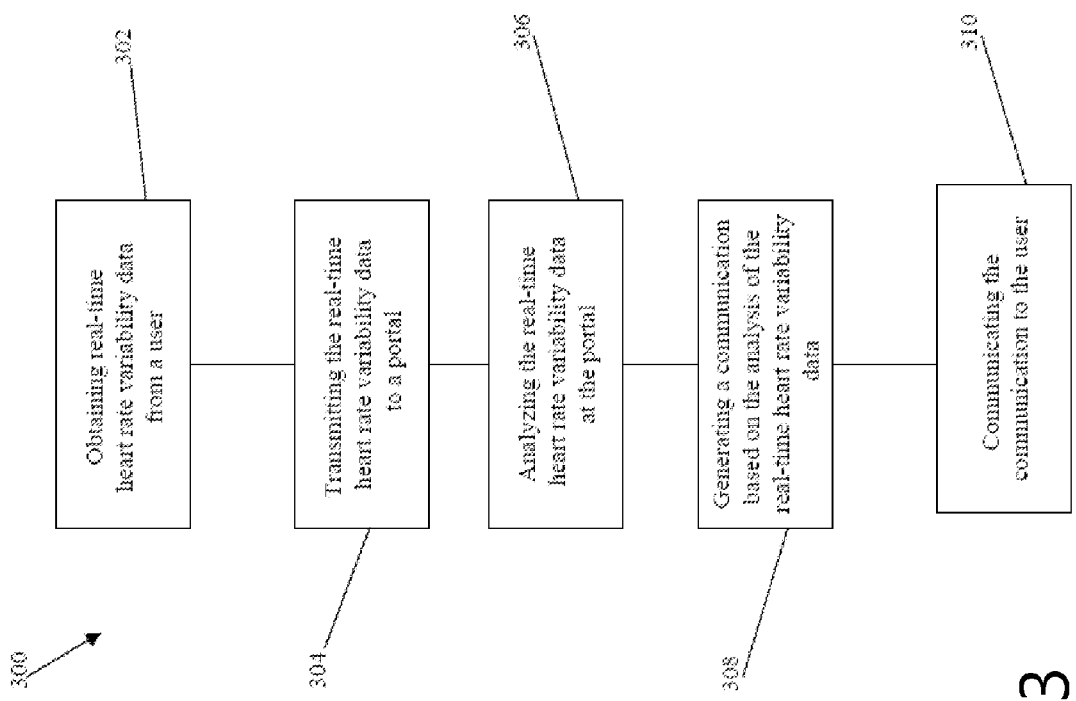
FIG. 3 is an exemplary flow chart in accordance with an embodiment.

An additional exemplary flow chart 300 in accordance with another embodiment is illustrated in FIG. 3. At step 302, real-time HRV data is obtained for a user using one or more of the devices discussed above.

At step 304, the real-time HRV data is transmitted to a web portal over a communication network.

At step 306, the real-time HRV data is analyzed, typically at a server for the web portal.

At step 308, based on the analysis of the real-time HRV data, a communication is generated for the user. The communication is an advertisement or a personalized content based on the analysis of the real-time HRV data. At block 310, this communication is communicated to the user. Preferably, the communication is transmitted to the user is a similar fashion as the transmission of the real-time HRV data. Alternatively, the communication is sent to the user using another communication means such as email, text-message to a mobile telephone or personal digital assistant ("PDA"), postal mail, or the like.

In one embodiment, the communication is delivered to the user while the user is in a health conscious frame of mind. The user is receptive to the information since the user is in a physiological improvement frame of mind, e.g., health conscious. While the user in this frame of mind, the communication may have its greatest impact on the user, especially if advertisement is for a product or service to be purchased by the user. The advertisement or personalized content may also have a link, telephone number or other mechanism for obtaining the product or service in the advertisement or personalized content.

In one embodiment, a person may exercise on a treadmill that is in communication with the web portal, thereby conveying real-time physiological data for the person to the web portal for analysis or generation of a communication. Based on the real-time physiological data, it may be determined that the person is slightly overweight and the communication is an advertisement for a diet program that has been especially created for a person of a particular sex, age, mass, physical ability and cardio status. The advertisement may also has a link which allows the person to purchase or otherwise access the diet program information.

Figure 4:
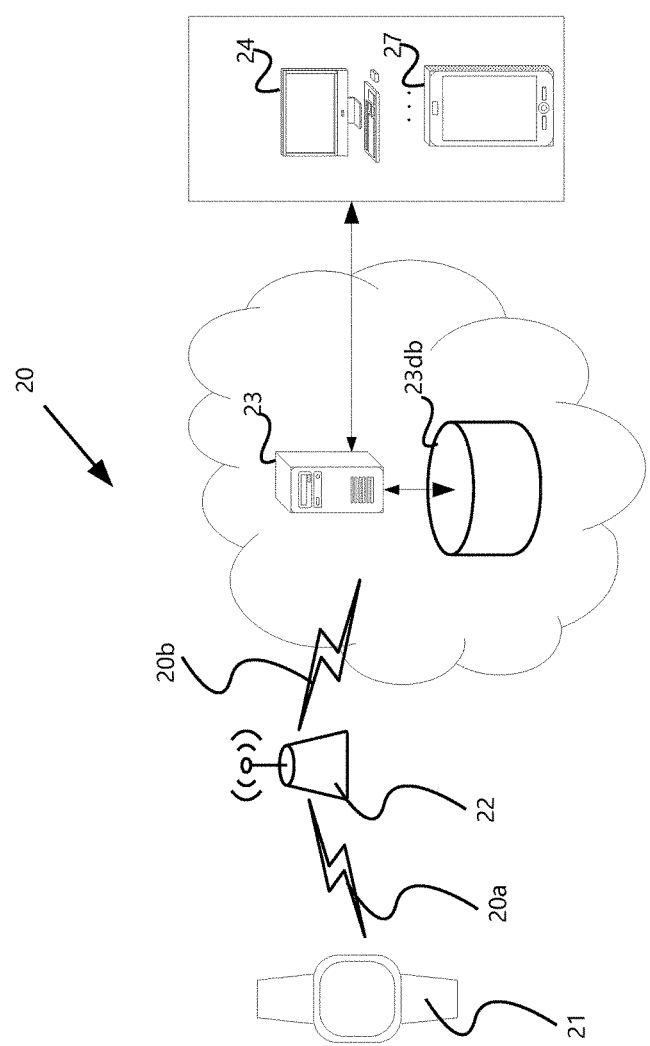
FIG. 4 is an exemplary illustration of a system in accordance with an embodiment.

FIG. 4 is an illustration of one system 20 of communicating a user's real-time physiological data with the web portal and communicating a communication to the user. The system 20 includes a physiological monitoring device 21 that obtains real-time physiological data for a user and transmits that transmission 20a to an antenna 222 of a communication network for communication 20b to a server 23 for a web portal 24. Then, a communication is sent to the user for display on a computing device, such as PDA 27.

Figure 5:
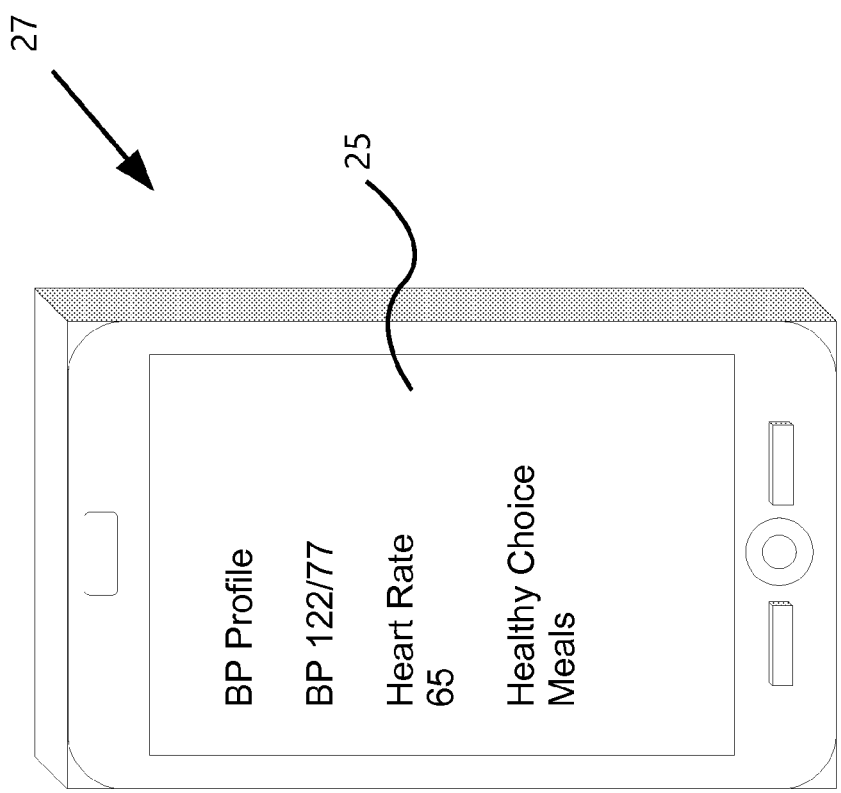
FIG. 5 is an illustration of an example communications device in accordance with an embodiment.

As shown in FIG. 5, on a display 25 of a PDA 27, a communication may be sent to a user for Healthy Choice Meals based on the user's real-time blood pressure data.

Figure 6:
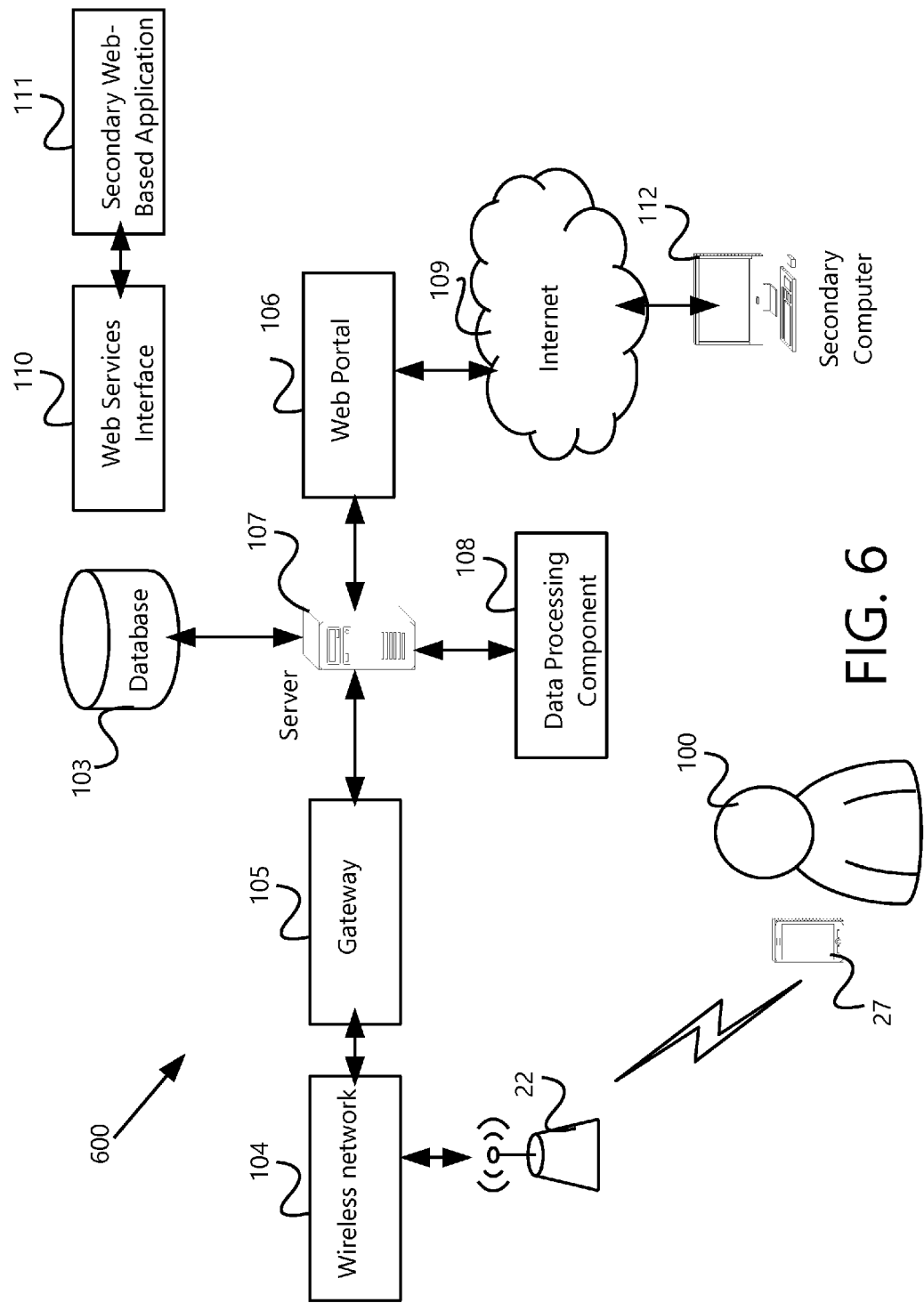
FIG. 6 is an exemplary illustration of a system in accordance with an embodiment.

A more detailed system of the present invention is shown in FIG. 6. The system 600 may operate the computing device 27 (such as a watch or phone) to transmit real-time physiological date from a user through a wireless network 104 to a web portal 106 hosted on an Internet-based server 107. A secondary computer 112 accesses the web portal 106 through the Internet 109. A wireless gateway 105 connects to the wireless network 104 and receives and delivers data from and to the device 27. The wireless gateway 105 additionally connects to the server 107 that includes a database 103 and a data-processing component 108 for, respectively, storing and analyzing the data. The server 107, for example, may include multiple computers, software pieces, and other signal-processing and switching equipment, such as routers and digital signal processors. The wireless gateway 105 preferably connects to the wireless network 104 using a TCP/IP-based connection, or with a dedicated, digital leased line (e.g., a frame-relay circuit or a digital line running an X.25 or other protocols). The server 107 also hosts the web portal 106 using conventional computer hardware (e.g. computer servers for both a database and the web site) and software (e.g., web server and database software). Additionally, the server 107 includes a web services interface 110 that transmits data using an XML-based web services link to a secondary, web-based computer application 111. This application 111 is preferably a data-management system operating at a health clinic.

For web advertising, an ad is usually a banner, a graphic image of a designated pixel, size and byte size limit. It is usually an animated GIF (a series of pictures displayed in a repetition that appears to move). Banners and other special advertising that include an interactive element, a high quality audio or visual element beyond the usual are known as rich media. Multiple locations on a given page may be available for ads.

The advertising medium type includes HTML text with tags that control characteristics (color size font design and table layout), small photos and art (GIF Graphic Interchange Format), banner ad, higher quality larger photographs (.jpg Joint Photographic Expert Group), simple audio (.wav) or synthesized music, streaming media audio (QUICKTIME, REAL Audio or WINDOWS Media Player).

An ad space is a sellable space on a web page that is reserved for ads. A group of spaces within a web site that share the same characteristics can be sold as an ad space group so that an ad purchase can be made for the group of spaces.

A banner is an advertisement in the form of a graphic image that is located across a top of a web page or is positioned in a margin or other space reserved for ads. Banner ads are usually GIF Graphics Interchange Format images that load quickly. Size limits on the file are made so that the ad file will display quickly. Most ads are animated GIF's since animation has been shown be attractive to users. Size ranges form 1 or 3 k to 70 or 90 k for animated GIF's. Most banners are 468 pixels wide by 60 pixels high. Smaller sizes include 125 by 125 and 120 by 90 pixels. Banner sizes have been established as standard sizes by the Internet Advertising Bureau (IAB).

A browser is an application program that provides a way to look at and interact with all the information on the World Wide Web. The word "browser" seems to have originated prior to the Web as a generic term for user interfaces that let you browse text files online. The first Web browser with a graphical user interface was invented (Mosaic, in 1992), the term seemed to apply to Web content, too. Technically, a Web browser is a client program that uses the Hypertext Transfer Protocol (HTTP) to make requests of Web servers throughout the Internet on behalf of the browser user. Parts of Mosaic went into the first widely used browser, Netscape Navigator, and Microsoft Internet Explorer. With a few exceptions such as Opera, these Navigator and Internet Explorer browsers are the only two browsers that the vast majority of Internet users have today. Online services, such as America Online, CompuServe, and Prodigy, had their own browsers, but now offer the customized versions of Netscape (Mozilla) or Microsoft browser. The newer version of these two browsers have the ability to run applet programs in Java™ or Active X extensions to HTML.

Caching is to speed up viewing and save bandwidth, a users browser with an internal cache, network cache servers and proxy servers save recently viewed files to avoid having to resend files before each view. Using a cache of pages in a cache server or the user's computer means that some ad views won't be known by the ad counting programs and is a source of concern. Although preventing caching gives a more accurate count, specifying no caching for all pages means that users will have slower time to view from each click, which is an action that requests the view of a web page. According to ad industry recommended guidelines from FAST, a click is "when a visitor interacts with an advertisement." This does not apparently mean simply interacting with a rich media ad, but actually clicking on it so that the visitor is headed toward the advertiser's destination.

A clickthrough is what is counted by the sponsoring site as a result of an ad click. In practice, click and clickthrough tend to be used interchangeably. A clickthrough, however, seems to imply that the user actually received the page instead of request only. Some advertisers are willing to pay only for clickthroughs rather than for ad impressions.

Click rate is the percentage of ad views that resulted in clickthroughs. A clickthrough is an indication of the ad's effectiveness and it results in the viewer getting to the advertiser's web site where other messages can be provided. A click to an immediate product order window can lead to a quick sale. Evaluation of clickthrough based on the campaign objectives, how enticing the banner message is, how explicit the message is (a teaser message is more likely to be clicked), audience/message matching, how new the banner is, how often it is displayed to that particular user. Reports n general, show click rates for high-repeat, branding banners vary from 0.15 to 1%. Ads with provocative, mysterious, or other compelling content can induce click rates ranging from 1 to 5% and sometimes higher. The click rate for any given ad tends to shrink upon repetition.

A cookie is a file on a web user's hard drive (it's kept in one of the subdirectories under the browser file directory) that is used by web sites to record data about the user. Multiple cookies may come from the same website. There may be a cookie that is associated with a specific individual session. Cookies help control multiple ad sequences by telling the web page server which ad the user has just seen so that a different ad will be rotated into the next page view.

A domain name locates an organization or other entity on the Internet. For example, the domain name for instance <www.miowatch.com> locates an Internet address at Internet point. The "com" part of the domain name reflects the purpose of the organization or entity (in this example, "commercial") and is called the top-level domain name. The "miowatch" part of the domain name defines the organization or entity and together with the top-level is called the second-level domain name.

A hit is the sending of a single file to a browser. The file type can be an HTML file, an image, an audio file, or other. Since a single web page request can have delivered with it a number of individual files, the number of hits from a site is a not an accurate indication of its actual number of visitors. It can be an indicator of traffic flow to the website but his is confused by proxy and cache servers that share frequently viewed files at a location on the Internet.

HTML (Hypertext Markup Language) is the set of "markup" symbols or codes inserted in a file intended for display on a World Wide Web browser. The markup tells the Web browser how to display a Web page's words and images for the user.

An IP address is a 32-binary digit number that identifies each sender or receiver of information that is sent in packet across the Internet. When one requests an HTML page or sends e-mail, the Internet Protocol part of TCP/IP includes the IP address in the message and sends it to the IP address that is obtained by looking up the domain name in the Uniform Resource Locator you requested or in the e-mail address you're sending a note to. At the other end, the recipient can see the IP address of the Web page requester or the e-mail sender and can respond by sending another message using the IP address it received.

The Internet Protocol (IP) is the method or protocol by which data is sent from one computer to another on the Internet. IP provides the routing mechanism. Each computer (known as a host) on the Internet has at least one IP address that uniquely identifies it from all other computers on the Internet. When you send or receive data (for example, an e-mail note or a Web page), the message is divided into little chunks called packets. Each of these packets contains both the sender's Internet address and the receiver's address. Any packet is sent first to a gateway computer that understands a small part of the Internet. The gateway computer reads the destination address and forwards the packet to an adjacent gateway that in turn reads the destination address and so forth across the Internet until one gateway recognizes the packet as belonging to a computer within its immediate neighborhood or domain. That gateway then forwards the packet directly to the computer whose address is specified.

In pay-per-click advertising, the advertiser pays a certain amount for each clickthrough to the advertiser's web site. The amount paid per clickthrough is arranged at the time of the insertion order.

In pay-per-lead advertising, the advertiser pays the source of for each sales lead generated, that is a finder's fee for every visitor that clicked on a site and then filled out a product interest form.

Pay-per-sale is the customary way to pay web, sites that participate in affiliate programs, such as those of Amazon.com and Beyond.com where the source of the sale gets a fee for each sale.

A splash page is a preliminary page that runs before the regular home page of a web site and usually promotes a particular site feature or provides advertising. A splash page is often new browser window that contains a rich media video or animation that jumps to the home page after a short period of time.

TCP (Transmission Control Protocol) is a method or protocol used along with the Internet Protocol (IP) to send data in the form of message units between computers over the Internet. While IP takes care of handling the actual delivery of the data, TCP takes care of keeping track of the individual units of data that a message is divided into for efficient routing through the Internet. TCP is known as a connection-oriented protocol, which means that TCP provides transport functions, which ensures that the total amount of bytes sent is received correctly at the other end. UDP is an alternate transport that does not guarantee delivery. UDP is widely used for real-time voice and video transmissions where erroneous packets are not retransmitted. TCP is responsible for ensuring that a message is divided into the packets that IP manages and is responsible for reassembling the packets back into the complete message at the other end.

In one embodiment, the system 20 is a SUN MICROSYSTEM workstation such as the SPARCstation brand workstation manufactured by Sun Microsystems of Mountain View, Calif. Note that the following discussion of various embodiments discussed herein will refer specifically to a series of routines which are generated in a high-level programming language (e.g., the PERL, JAVA, PYTHON, SMALLTALK interpretive and scripting languages) which is interpreted and/or executed in system 20 at run-time. These further are used in conjunction with the browser and server software available from NCSA, MOSAIC NETACAPE MICROSOFT and other SPYGLASS licenses including the specification of the appearance of displays in HTML. One skilled in the art appreciates that the following methods and apparatus may be implemented in special purpose hardware devices, such as discrete logic devices, large scale integrated circuits (LSI's), application-specific integrated circuits (ASIC's), or other specialized hardware. Other programming languages, C, BasicC, C++ and other Operating systems such as Unix, Posix, and variations of Linux platforms may be utilized.

Another embodiment Web Server platform comprises an IBM RISC System/6000 computer running the AIX (Advanced Interactive Executive) Operating System and a Web server program, such as Netscape Enterprise Server Version 2.0, that supports interface extensions. The platform also includes a graphical user interface (GUI) for management and administration. The various models of the RISC-based computers are described in many publications of the IBM Corporation, for example, RISC System 6000, 7013 and 7016 POWERstation and POWERserver While the above platform is useful, any other suitable hardware/operating system/Web server combinations may be used. Accordingly, the web server description here has equal application to apparatus having similar components and functions.

Figure 7:
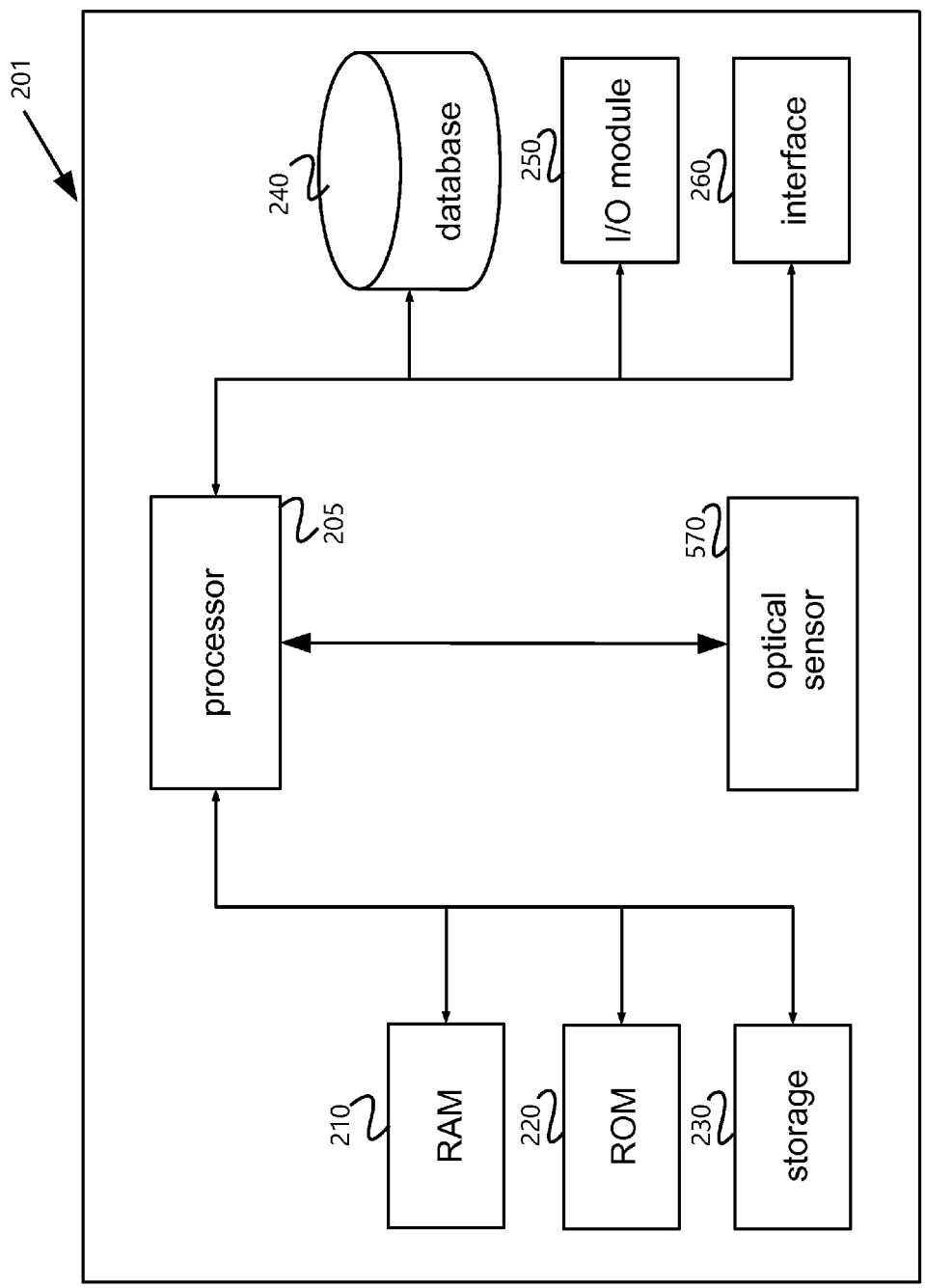
FIG. 7 is an exemplary illustration of system components in accordance with an embodiment.

FIG. 7 depicts an exemplary processor-based computing system 201 representative of the type of computing system that may be present in or used within the computing device 27 or serve 107 in an embodiment. The computing system 201 is exemplary only and does not exclude the possibility of another processor- or controller-based system being used in or with one of the aforementioned components.

In one aspect, system 201 may include one or more hardware and/or software components configured to execute software programs, such as software for storing, processing, and analyzing data. For example, system 201 may include one or more hardware components such as, for example, processor 205, a random access memory (RAM) module 210, a read-only memory (ROM) module 220, a storage system 230, a database 240, one or more input/output (I/O) modules 250, and an interface module 260. Alternatively and/or additionally, system 201 may include one or more software components such as, for example, a non-transitory computer-readable medium including computer-executable instructions for performing methods consistent with certain disclosed embodiments. It is contemplated that one or more of the hardware components listed above may be implemented using software. For example, storage 230 may act as digital memory that includes a software partition associated with one or more other hardware components of system 201. System 201 may include additional, fewer, and/or different components than those listed above. It is understood that the components listed above are exemplary only and not intended to be limiting.

Processor 205 may include one or more processors, each configured to execute instructions and process data to perform one or more functions associated with system 201. The term "processor," as generally used herein, refers to any logic processing unit, such as one or more central processing units (CPUs), digital signal processors (DSPs), application specific integrated circuits (ASICs), field programmable gate arrays (FPGAs), and similar devices, such as a controller. As illustrated in FIG. 2A, processor 205 may be communicatively coupled to RAM 210, ROM 220, storage 230, database 240, I/O module 250, and interface module 260. Processor 205 may be configured to execute sequences of computer program instructions to perform various processes, which will be described in detail below. The computer program instructions may be loaded into RAM for execution by processor 205.

RAM 210 and ROM 220 may each include one or more devices for storing information associated with an operation of system 201 and/or processor 205. For example, ROM 220 may include a memory device configured to access and store information associated with system 201, including information for identifying, initializing, and monitoring the operation of one or more components and subsystems of system 201. RAM 210 may include a memory device for storing data associated with one or more operations of processor 205. For example, ROM 220 may load instructions into RAM 210 for execution by processor 205.

Storage 230 may include any type of storage device configured to store information that processor 205 may need to perform processes consistent with the disclosed embodiments.

Database 240 may include one or more software and/or hardware components that cooperate to store, organize, sort, filter, and/or arrange data used by system 201 and/or processor 205. For example, database 240 may include information to that tracks physiological parameters, activity types and levels, and HRV for users based on embodiments herein. Alternatively, database 240 may store additional and/or different information. Database 240 may also contain a plurality of databases that are communicatively coupled to one another and/or processor 205, of may connect to further database over the network.

I/O module 250 may include one or more components configured to communicate information with a user associated with system 201. For example, I/O module 250 may include a console with an integrated keyboard and mouse to allow a user to input parameters associated with system 201, such as the identification of the user to independently track different users of the computing device (e.g., a watch shared by different users). I/O module 250 may also include a display including a graphical user interface (GUI) for outputting information on a monitor. I/O module 250 may also include peripheral devices such as, for example, a printer for printing information associated with system 201, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 260 may include one or more components configured to transmit and receive data via a communication network, such as the Internet, a local area network, a workstation peer-to-peer network, a direct link network, a wireless network, or any other suitable communication platform, such as Bluetooth. For example, interface 260 may include one or more modulators, demodulators, multiplexers, demultiplexers, network communication devices, wireless devices, antennas, modems, and any other type of device configured to enable data communication via a communication network.

Optical sensor 570 may allow the system 201 to determine if a user is inside or outside, or in a lighted versus darkened room. This may allow for further insights into the user's activity in conjunction with other sensors that detect motion or physiological attributes.

In one embodiment, the system may continuous test physiological parameters of a user, including periodic recording of heart rate variability, to assess stress level and physical fitness of users. The assessment may be carried out automatically during user's usual daily physical activity.

Figure 8:
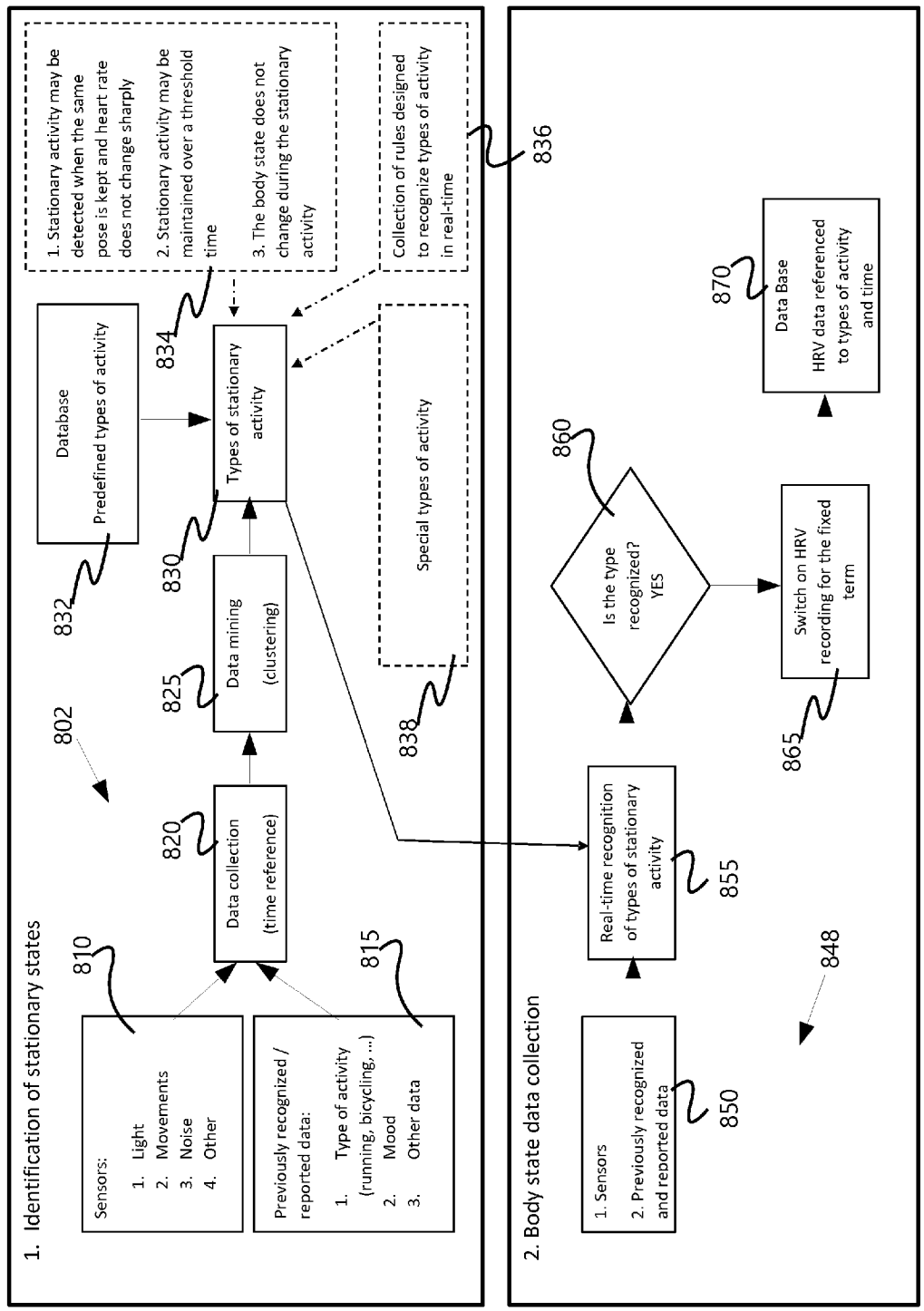
FIG. 8 is an exemplary flow chart in accordance with an embodiment.
Figure 9:
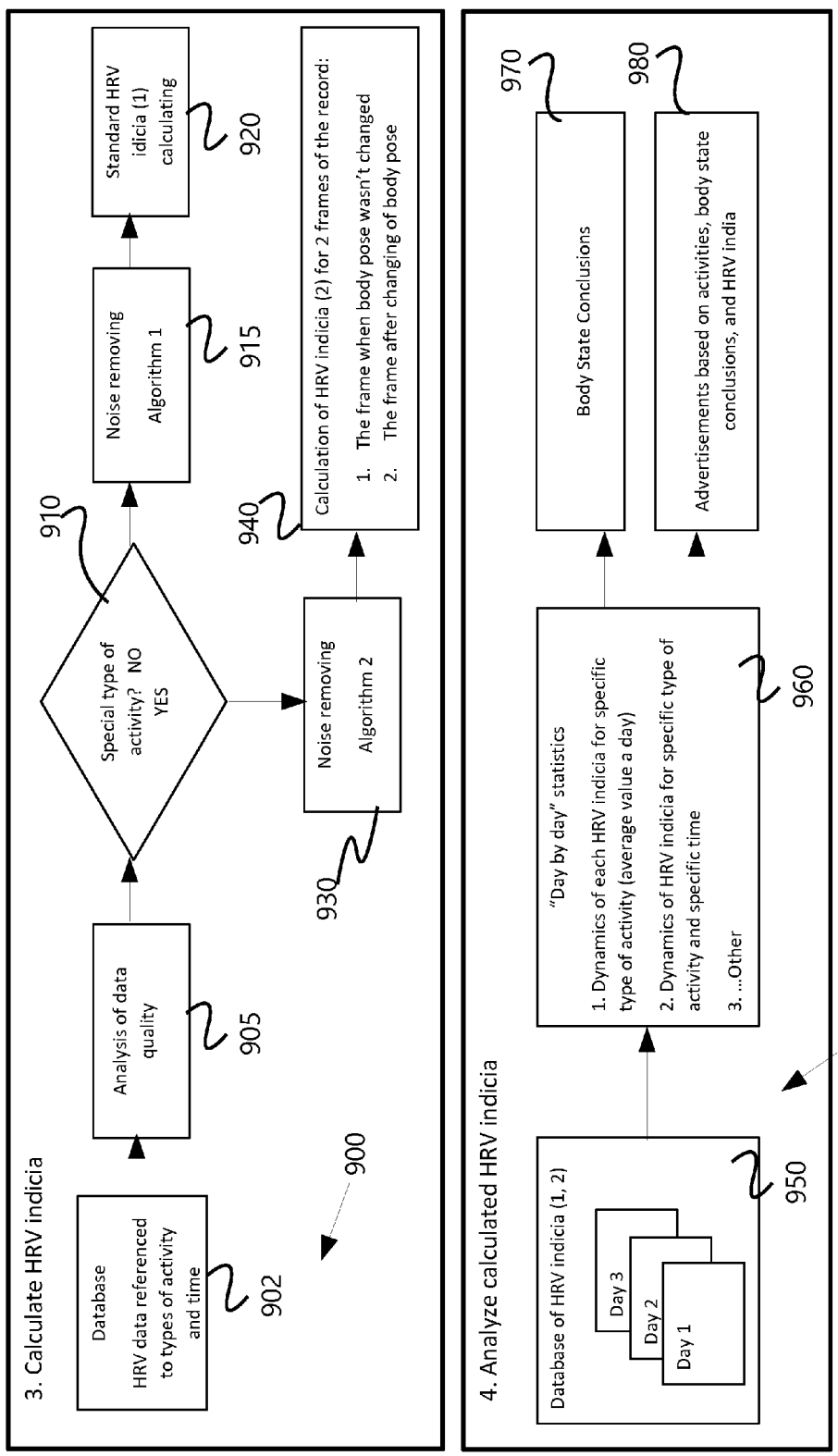
FIG. 9 is an exemplary flow chart in accordance with an embodiment.

FIGS. 8 and 9 include exemplary steps for continuously testing activity data and the physiological parameters of a user. FIG. 8 includes example steps for identifying stationary states of a user and for collecting data regarding body states of a user. At 802, exemplary steps related to detecting a stationary state are shown.

At step 810, various sensors in a computing device, such as a wrist-worn watch or bracelet, may detect light, movement, noise, or other environmental characteristics that may be used as sensed activity data. Sensors such as an optical sensor, piezoelectric sensor, accelerometer, and/or microphone, may make these detections. Other sensed characteristics may include temperature or temperature change. This may indicate that a user has, for example, transitioned from outdoors to indoors or vice versa. Another characteristic may be light frequency, which may inform the type of environment the user is in. For example, the light frequencies of fluorescent lighting differ from those of sunlight. Other data, such as the sound of typing, the sound of talking, or oxygen or blood flow levels consistent with various types of activity may be recorded via the various sensors.

At step 815, other activity data representative of user activities or other attributes may be input by the user and/or retrieved by a server. For example, through inputting activity data, the user may indicate an activity, such as running, cycling, swimming, hiking, or weight lifting is taking place by selecting an activity on their computing device. Other attributes, such as mood, may be input by the user, such as with respect to a social media profile. Age may also be input by the user, for use in adjusting HRV insights made by the system, since age and HRV are correlated.

The user may also indicate a location where they are present that provides insight into their activities, such as a restaurant location, a gym location, or a sporting event location. In one embodiment, the computing device uses GPS to collect this information. In still another embodiment, data regarding the apparel (e.g., clothes or shoes) of the user may be collected through user input or though wireless connection between the apparel and the computing device. The apparel worn may indicate the user's activity based on differences in purpose of work apparel, sleep apparel, and exercise apparel.

At step 820, the data from steps 810 and 815 may be collected on the computing device and/or a server that communicates with the computing device. This may include storing the data in a database with respect to a particular user identifier.

At step 825, the server may make determinations regarding the user's activity by analyzing patterns in the collected data, such as through cluster analysis-type data mining. Other techniques for machine learning, pattern recognition, and bioinformatics may be incorporated in addition or in the alternative. This may help remove or diminish the weight of outlier data and noise from the analysis. The cluster model may include algorithms based on both the sensor inputs of step 810 and the user inputs of step 815.

The analysis may include a comparison against predefined types of activity that are stored in a database 832. The database 832 may include predefined rules that allow the system to identify and recognize different activity types. Different activities may include sitting, television watching, driving, jogging, sleeping, eating, working at a desk, gardening, lifting weights, and more.

In one embodiment, the database may be continuously updated by the system to learn new patterns indicative of particular states based on both the step 810 and 815 data. The rules may be in flux based on user-verified activities. For example, at step 830, the system may collect new rules based on the determinations at step 825 and/or adjust existing predefined rules in database 832 based on a user's particular habits. For example, a particular user may have a proclivity for a certain activity type during a particular time period, so the rules may be adjusted specifically for that user to bias towards the activity type during the detected time period.

From those data-defined activities, particular stationary activity may be determined at step 830 in real time. The system may utilize rules at 836 to compare real-time data against historical patterns in the database at step 832. Various patterns and indicia may be analyzed to determine the stationary activity. For example, as shown in step 834, stationary activity may be indicated when the same pose is kept and heart rate does not change abruptly. A consistent heart rate and body location tend to indicate stationary activity.

This may be analyzed to determine the user is stationary based on one or more time thresholds. For example, the heart rate and movement of a user may be tracked over 60 seconds, 128 seconds, and 256 seconds in one embodiment. The different time thresholds may allow for determining different types of stationary activity if the body state does not change over those time thresholds. In another embodiment, recording of user heart rate and movement continues during an activity even after that specific activity has been recognized. This recorded data may be utilized to further develop the pattern recognition involved in identifying the activity again in the future.

Other special types of activity and stationary activities may be determined at step 838. For example, a sharp change in body pose, such as from laying down to standing up in a short time (e.g., less than five minutes) may be detected.

Additional exemplary body state data collection steps are shown at 848. At step 850, sensors and previously recognized and/or reported data may be utilized by the system in analyzing body state.

At step 855, the system may recognize types of activity, including stationary activity, in real time. If a particular state is recognized at step 860, then HRV recording may be switched on at step 865. Other types of data may also be collected as step 865, such as blood pressure. Based on the recorded HRV and/or other collected data, a particular state (such as stress level) may be verified and/or a determination may be made regarding when the state is ending. Additionally, HRV data collection may allow for analysis of quality of rest and other characteristics within a stationary state.

Continuing at FIG. 9, exemplary steps for calculating HRV indices are illustrated at 900. At step 902, the database is queried to obtain the recorded HRV data and reference the data to activity types and timing thresholds. The data may be analyzed at step 905 to determine if a special type of activity is present, such as a user sitting up or rolling over at 910.

If a special type of activity is not detected, then the system may apply a first noise removing algorithm at 915. Then at step 920, the system may calculate HRV indicia (also referred to herein as HRV indexes).

Alternatively, if a special type of activity is detected, the system may perform a different noise removing algorithm at step 930 and then, at step 940, calculate HRV indicia separately according to when the body position or pose was unchanged and after the body position or pose changed. The noise removing algorithm may be specific to the detected type of activity and/or analog sensor relied on because different activities may tend to introduce different types and/or levels of noise. Thus, recognizing an activity also may cause the system to apply a more suitable noise algorithm, meaning that the number of noise algorithms may equal the number of activities in one embodiment.

These calculated HRV indicia are then further analyzed, such as through the exemplary steps shown at 945.

For example, at step 950 HRV indicia for multiple days may be analyzed to generate insights for the user. As shown at 960, day by day statics may include values representative of how much the user performs each specific activity type per day. The user may be able to use an app, web interface, or display on a watch to see specific activity statistics for each day in one embodiment. In another embodiment, the statistics may be presented as bar charts, and bars may represent activity levels for each activity. Bar graphs for multiple days may be overlaid on top of one another to easily visualize changes per day. The activity levels may be given scores within the range of 0 to 100 to give a user a numeric reference to strive towards.

In another embodiment, the user may be able to select a particular activity and day and see specific details about that activity, such as heart rate, duration, location, and others.

At step 970, the system may also present conclusions to the user regarding the user's body state. For example, the system may determine that the user's body state is good, strained, or poor in one embodiment. These insights may allow the user to better tailor activity regimens (e.g., exercise) such that their body state is not poor or strained.

In another embodiment, the conclusion indicates that the user has one of a variety of physiological characteristics, including a high or low blood pressure, high or low stress level, underweight or overweight, rapid heartbeat or arrhythmia, possibility of disease, or improving health compared to other similar users.

At step 980, the system may present advertisements to the user in conjunction with the statistics and/or conclusions. For example, if the user is having trouble sleeping, as determined by their sleep state being below an activity threshold, fluctuations of HRV during sleep, and/or sudden movements during sleep, an advertisement for sleep assistance product may be presented. Similarly, if the daily levels for exercising are low, the user may be presented with gym advertisements. If the activity level for running begins to increase but running causes a HRV to change more than a threshold amount over a time frame, advertisements directed to new runners may be displayed.

Other embodiments of the aforementioned systems and methods will be apparent to those skilled in the art from consideration of the specification and practice of this disclosure. It is intended that the specification and the aforementioned examples and embodiments be considered as illustrative only, with the true scope and spirit of the disclosure being indicated by the following claims.

What is claimed is:

1. A system for providing user insights based on heart rate variability, the system comprising:
   a wrist-worn device that obtains real-time physiological data including heart rate variability data from a user, obtains activity data from a user, and transmits the real-time physiological data and activity data; and
   a processor that performs stages including:
      receiving the activity data;
      analyzing the activity data to determine whether the user is engaged in one of a plurality of stationary activities;
      in response to determining the user is engaged in one of the plurality of stationary activities, receiving and recording the real-time physiological data including the heart rate variability data;
      calculating a first heart rate variability indicia;
      transmitting a conclusion to the user that is derived at least in part from the first heart rate variability indicia, wherein the analysis of the plurality of real-time physiological data for the user includes comparing a heart rate variability pattern to the heart rate variability data over multiple days to demonstrate that the user has improved their health at a greater pace than a group of similar aged users that are tracked by the server, and the conclusion represents the user's status as compared to the group of similar aged users.

2. The system of claim 1, wherein the processor further determines that the user experiences a change in body pose based on the activity data, and calculates a second heart rate variability indicia subsequent to the change.

3. The system of claim 1, wherein the transmitted conclusion indicates a change in stress level.

4. The system of claim 1, wherein the transmitted conclusion indicates the user is stressed.

5. The system of claim 1, wherein the processor is located in a server that is remote from the wrist-worn device.

6. The system of claim 1, wherein the wrist-worn device gathers at least some of the activity data in real time based on an accelerometer.

7. The system of claim 1, wherein the wrist-worn device gathers at least some of the activity data in real time based on detecting light.

8. The system of claim 1, wherein the processor further selects a noise-cancelling algorithm based on which of the stationary activities the user is engaged in.

9. A method for communicating personalized health content to a user, the method comprising:
   obtaining activity data for the user from a wrist-worn device;
   obtaining real-time physiological data for the user from the wrist-worn device;
   detecting an action based on the activity data,
   in response to the detected action, receiving and recording the real-time physiological data, including heart rate variability data;

analyzing the heart rate variability data to determine an activity's effect on the user's body state; and communicating a conclusion regarding stress or health based on the real-time heart rate variability data and body state, wherein analyzing the heart rate variability data includes comparing a heart rate variability pattern to the heart rate variability data over multiple days to demonstrate that the user has improved their health at a greater pace than a group of similar aged users that are tracked by the server, and the conclusion represents the user's status as compared to the group of similar aged users.

10. The method according to claim 9, further including obtaining a real-time heart rate for the user and utilizing the heart rate in determining the conclusion to communicate.

11. The method according to claim 9, wherein the wrist-worn device is a watch.

12. The method according to claim 9, wherein transmitting the heart rate variability data comprises transmitting the real-time physiological data over the Internet to a server.

13. The method according to claim 9, wherein the real-time physiological data for the user includes body-fat, glucose values, and calories burned for the user.

14. The method according to claim 9, further including sending an advertisement to the user that is personalized for the user based on the analysis of the real-time physiological data and heart rate variability data.

15. The method according to claim 14, wherein the advertisement is for a medicine or supplement that addresses a health condition determined by the analysis of the real-time physiological data and heart rate variability data.

16. The method according to claim 9, further including receiving data from a social media profile and using the received data from the social media profile in determining the conclusion.

17. A system for communicating personalized content to a user based on the user's real-time physiological data, the system comprising:

a wrist-worn device that obtains real-time physiological data for a user, receives activity data for a user, and transmits the real-time physiological data and activity data, wherein the real-time physiological data includes heart rate variability data; and a processor that performs stages including:
  receiving the activity data;
  determining that the real-time physiological data should be received based on the activity data;
  receiving the real-time physiological data;
  analyzing the real-time physiological data to determine a health status to communicate the user regarding based on the real-time physiological data; and
  communicating the health status to the user, wherein analyzing the real-time physiological data includes comparing a heart rate variability pattern to the heart rate variability data over multiple days to demonstrate that the user has improved their health at a greater pace than a group of similar aged users that are tracked by the server, and the health status represents the user's status as compared to the group of similar aged users.

18. The system according to claim 17, further including a communications device that interfaces with the wrist-worn device, the communications device sending the real-time physiological data over the Internet to the processor.

19. The system according to claim 17, wherein the health status relates to stress and includes an advertisement for a medicine or supplement selected based on the analysis of the real-time physiological data.

* * * * *